United States Patent
Anker

(10) Patent No.: US 8,383,612 B2
(45) Date of Patent: Feb. 26, 2013

(54) USE OF MEGESTROL ACETATE FOR IMPROVING HEART FUNCTION AND THE TREATMENT OF HEART INSUFFICIENCY

(75) Inventor: Stefan Anker, Berlin (DE)

(73) Assignee: Par Pharmaceuticals, Inc., Spring Valley, NY (US)

( * ) Notice: Subject to any disclaimer, the term of this patent is extended or adjusted under 35 U.S.C. 154(b) by 723 days.

(21) Appl. No.: 11/667,899

(22) PCT Filed: Dec. 1, 2005

(86) PCT No.: PCT/EP2005/012843
§ 371 (c)(1),
(2), (4) Date: Sep. 24, 2007

(87) PCT Pub. No.: WO2006/058748
PCT Pub. Date: Jun. 8, 2006

(65) Prior Publication Data
US 2008/0139521 A1 Jun. 12, 2008

(30) Foreign Application Priority Data
Dec. 1, 2004 (EP) .................................... 04028474

(51) Int. Cl.
*A01N 45/00* (2006.01)
*A61K 31/56* (2006.01)

(52) U.S. Cl. ........................................ 514/178; 514/171

(58) Field of Classification Search .................. 514/178, 514/171
See application file for complete search history.

(56) References Cited

U.S. PATENT DOCUMENTS

| 4,370,321 A | 1/1983 | Greaney et al. |
| 5,144,017 A | 9/1992 | LaBella et al. |

FOREIGN PATENT DOCUMENTS

| WO | WO 97/25028 | * | 7/1997 |
| WO | WO97/25028 | * | 7/1997 |
| WO | WO 03/086354 | * | 10/2003 |
| WO | WO03/086354 | * | 10/2003 |
| WO | WO2004/041289 | * | 5/2004 |
| WO | WO 2004/041289 | * | 5/2004 |

OTHER PUBLICATIONS

Thurliman et. al., European Journal of Cancer (1977) 35:1017-1024.*
Remme et. al. (European Heart Journal (2001) 22:1527-1560).*
Thurlimann et. al. (European Journal of Cancer (1997) 33:1017-1024).*
Isaac, J.H., "Megestrol acetate treatment of failure to thrive in congenital heart disease," *Pediatric Cardiology*, Sep. 1999, vol. 20, No. 5, p. 350.
Kim, R.-S. et al., "Progesterone derivatives that bind to the digitalis receptor: structure-activity relationships," *Molecular Pharmacology*, 1980, vol. 18, No. 3, pp. 402-405.
Thurlimann, B. et al., "Formestane Versus Megestrol Acetate in Postmenopausal Breast Cancer Patients After Failure of Tamoxifen: a Phase III Prospective Randomised Cross Over Trial of Second-line Hormonal Treatment (SAKK 20/90)," *European Journal of Cancer*, Jun. 1997, vol. 33, No. 7, pp. 1017-1024, Pergamon Press, Oxford, GB.

* cited by examiner

*Primary Examiner* — Marcos Sznaidman
(74) *Attorney, Agent, or Firm* — Saliwanchik, Lloyd & Eisenschenk

(57) ABSTRACT

The present invention relates to improving the heart function, the survival and/or the treatment of heart insufficiency using megestrol acetate (Megace®; MA) in patients with heart insufficiency and after a myocardial infarction.

19 Claims, 7 Drawing Sheets

USE OF MEGESTROL ACETATE FOR IMPROVING HEART FUNCTION AND THE TREATMENT OF HEART INSUFFICIENCY

This application is a National Stage Application of International Application Number PCT/EP2005/012843, filed Dec. 1, 2005; which claims priority to European Application No. 04028474.7, filed Dec. 1, 2004.

The present invention relates to the improved treatment of patients having suffered from myocardial infarction and/or of patients with heart failure using megestrol acetate (Megace®; MA), in particular using megestrol acetate oral suspension (Megace®), more precisely using the advanced microcrystalline formulation of megestrol acetate oral suspension, namely Megace® ES.

BACKGROUND OF THE INVENTION

Cardiovascular illness is a major health care problem in modern society. Coronary artery disease often leads to myocardial infarction and heart failure. In the USA, chronic heart failure is the most frequent reason for hospitalisation in people over the age of 65.

Chronic heart insufficiency (CHI) is a complex syndrome and influences many systems of the body. The most common reason for CHI in elderly is the coronary heart disease [Ho K K L, Anderson K M, Kannel W B, et al. Survival after the onset of congestive heart failure in Framingham heart study subjects. Circulation 1993; 88: 107-115]. In case of CHI, a series of pathophysiological modifications of haemodynamic, metabolic or functional type occur [Anker S D, Coats A J S. Metabolic, functional and haemodynamic staging for CHF. Lancet 1996; 348: 1530-1531].

The prevalence of CHI in the population reaches approximately 0.3-2% in total [Cowie M R, Mosterd A, Wood D A, Deckers J W, Poole-Wilson P A, Sutton G C, et al. The epidemiology of heart failure. Eur Heart J 1997; 18:208-225]. Worldwide, the number is therefore estimated to be 15 million patients. The prevalence of CHI increases with age and reaches more than 10% in persons being older than 80 years [Kannel W B, Belanger A J. Epidemiology of chronic heart failure. Am Heart J 1991; 121: 951-957]. Predisposing factors of CHI are hypertonus, diabetes mellitus, smoking, adipositas and hyperlipidemia.

Megestrol acetate (MA, Megace®) is a synthetically produced derivative of the naturally occurring steroid hormone progesterone. Megace® is a white, crystalline substance having the chemical name 17-α-acetoxy-6-methylpregna-4,6-diene-3,20-dione ($C_{24}H_{32}O_4$) and a molecular weight of 384.5. Megestrol acetate has the following formula:

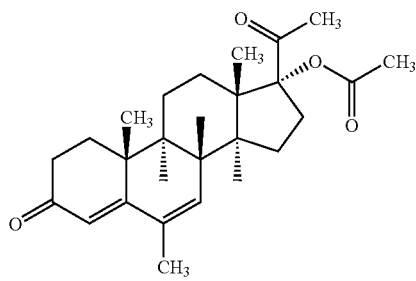

Megace® is an orally active solution and is primarily excreted via the kidneys. The bio-availability is not completely elucidated. Megestrol acetate is an appetite stimulant that acts by a still unknown mechanism. Initially, Megace® was used for the inhibition of malignant post-menopausal hormone dependent tumours of the breast [Gregory E J, Cohen S C. Megestrol acetate therapy for advanced breast cancer. J Clin Oncol 1985; 3:155-160. Benghiat A, Cassidy S A. Megestrol acetate in the treatment of advanced post-menopausal breast cancer. Eur J Surg Oncol 1986 12: 43-45, Goss P E. Pre-clinical and clinical review of vorozole, a new third generation aromataose inhibitor. Report. Breast Cancer Res Tr 1998; 49: S59-S65] and the prostate [Keller J, White J M. A phase III randomised comparative trial of megestrol acetate v. diethylstilbestrol in stage D2 prostatic cancer. Preliminary results. Proc Am Soc Clin Oncol 1986, 5:421. Bonomi P, Pessis D, Bunting N, et al. Megestrol acetate used as primary hormonal therapy in stage D prostatic cancer. Semin Oncol 1985; 12 (Suppl 1): 36-39]. While using it, an increase of weight and an appetite stimulation was discovered as side effects. Initially, a dose of 30 mg/d [Stoll B A. Progestin therapy of breast cancer: comparison of agents. Br Med J 1967; 3: 338-341] was used. In 10% of the patients an increase of weight of at least 5% was observed after six weeks in case of a dose of 60-180 mg/d [Alexieva-Figusch J, Van Glise H A. Progestin therapy in advanced breast cancer: Megestrol acetate—An evaluation of 160 treated cases. Cancer 1980; 46: 2369-2372]. Further studies confirmed the appetite stimulating effect [Tchekmedyian N S, Tait N, Moody M, Aisner J. High dose megestrol acetate: a possible treatment for cachexia. JAMA 1987; 257: 1195-1198]. In case of a later standard dose of 160 mg Megace®/d in nearly one third of the patients an increase of the weight was found [Keller J, White J M. A phase III randomised comparative trial of megestrol acetate v. diethylstilbestrol in stage D2 prostatic cancer. Preliminary results. Proc Am Soc Clin Oncol 1986, 5:421. Bonomi P, Pessis D, Bunting N, et al. Megestrol acetate used as primary hormonal therapy in stage D prostatic cancer. Semin Oncol 1985; 12 (Suppl 1): 36-39, Tchekmedyian N S, Tait N, Moody M, et al. Appetite Stimulation with megestrol acetate in cachectic cancer patients. Sem Oncol 1986; (Suppl 4): 37-43]. In higher dose of 1600 mg Megace®/d, in 81% of all patients (>2 kg, median 5.5 kg) and in more than 90% of the patients with mama carcinoma, an increase of weight was reached. Thus, a dosage and time dependent effect of Megace® exists, wherein the dosage dependent effect is not yet statistically proven. For further information regarding Megace® and dosage options, see, for example, http://www.medsafe.govt.nz/profs/Datasheet/m/Megacetab.htm Megace® has been used for several years successfully in cachexia of patients having mamma carcinoma or other malignant tumours. In Germany, the medicament is only registered for the therapy in progressed mamma carcinoma. For a specific therapy in patients with mama carcinoma in phase IV for improving the quality of life the dosages 160 mg/d, 800 mg/d and 1600 mg/d were compared in the CALGB-study and 160 mg/d was found as the optimal dosage [Komblinth A B, Hollis D R, Zuckerman E, et al. Effect of megestrol acetate on quality of life in a dose-response trial in woman with advanced breast cancer. J Clin Oncol 1993; 11: 2081-2089].

In studies with patients having AIDS-cachexia, von Roenn et al. [Von Roenn J H, Armstrong D, Kotler D P, et al. Megestrol Acetate in patients with AIDS-related cachexia. Ann Inter Med 1994; 121: 393-399] studied 232 patients with MA in different dosages: 100 mg/d, 400 mg/d, and 800 mg/d. In this study, 800 mg/d was found as optimal dosage. For a human, a dosage of 13.3 mg/kg/d is recommended. It could be shown that the most reasonable dosage for the therapy of cachexia (best weight increase in relation to side effects) in the human is 800 mg/d (corresponds to approximately 13 mg/kg/d at 60 kg body weight) as overall dosage in one or two applications [Oster M H, Enders S R, Samuels S J, et al. Megestrol acetate in patients with AIDS and Cachexia. Ann Intern Med 1994; 121: 400-408, Von Roenn J H, Armstrong D, Kotler D P, et al. Megestrol Acetate in patients with AIDS-related cachexia. Ann Inter Med 1994; 121: 393-399].

Recently, a novel substance herein below designated as "novel Megace®" has been introduced that is also designated as "Megace® ES". Novel Megace® essentially is the same medication as the commonly used megestrol acetate, but having a micro-crystalline structure which significantly improves resorption. Both oral suspensions contain the same active agent, however, Megace® ES has a different formulation why resorption is significantly improved. Par Pharmaceutical Companies, Inc. manufactures this advanced formulation, as disclosed in the PCT application WO 03/086354 A1. The improvement is caused by a nanoparticulate composition comprising megestrol acetate and preferably at least one surface stabilizer associated with the surface of the drug. These nanoparticulate megestrol particles have an effective average particle size of less than about 2000 nm. This advanced formulation, in a preferred embodiment thereof, utilises NanoCrystal™ Dispersion technology to improve the bioavailablity of the drug, compared to currently available formulations of the product, as disclosed in WO 04/050059 as a low viscosity liquid dosage form comprising particles of an active agent, a surface stabilizer, and a pharmaceutically acceptable excipient, carrier, or a combination thereof, wherein the active agent particles have an effective average particle size of less than about 2 microns and the dosage form has a viscosity of less than about 2000 mPa·s at a shear rate of 0.1 (1/s). NanoCrystal® Dispersion is a trademark of Elan Corporation, plc, Dublin, Ireland. Megace® is a registered trademark of Bristol-Myers Squibb Company licensed to Par Pharmaceutical, Inc. The U.S. Food and Drug Administration (FDA) has approved Megace® ES for the treatment of anorexia, cachexia, or an unexplained, significant weight loss in patients with a diagnosis of acquired immunodeficiency syndrome (AIDS). Recent data have shown that the bioavailability of the original formulation is reduced substantially when taken on an empty stomach. With Megace® ES, this reduction in bioavailability is minimized in the fasted state, resulting in improved bioavailability in patients who have not eaten. Megace® ES 625 mg/5 ml and megestrol acetate oral suspension 800 mg/20 ml are bioequivalent in a fed state. The effect of novel Megace® appears to be faster than compared to the initial Megestrol acetate (herein designated as "old" (common) Megace®).

For Megace®, anti-androgene, anti-estrogene and small glucocorticoid-similar effects are assumed [Alexieva-Figusch J, Van Glise H A. Progestin therapy in advanced breast cancer: Megestrol acetate—An evaluation of 160 treated cases. Cancer 1980; 46: 2369-2372].

The standard therapy with medicaments in CHI consists in general in particular in the application of diuretics, ACE-blockers, optionally angiotensin, Il-receptor-antagonists, beta-blockers, and/or aldosteron-antagonists as well as medicaments for the prophylaxis and therapy of arrhythmias and angina pectoris. In addition, increasingly pace markers and implantable defibrillators are used. In patients with most severe CHI, surgical therapies with assist devices and heart transplantations are taken into account. A main aim of the therapy is, to improve life expectancy and life quality of the patients.

In cases of severe CHI the one year mortality in earlier studies despite therapy with vasodilators and digitalis reached 52%, in cases of additional application of an ACE-blocker still 36% per year [The CONSENSUS Trial Study group. Effects of enalapril on mortality in severe congestive heart failure: results of the Cooperative North Scandinavian Enalapril Survival Study (CONSENSUS). N Engl J Med 1987; 316: 1429-1435]. Despite further improved therapies including ACE-blockers and Beta-blockers, CHI of intermediate severity (New York Heart Association Class II-III) is today still related to a one year mortality of approximately 15-30% [Braunwald E (ed), et al. Heart Disease. A textbook of cardiovascular medicine. $6^{th}$ edition. WB Saunders Company 2001; chapter 17: 546-547, Johnson D, Jin Y, Quan H, et al. Beta-Blockers and angiotensin-converting enzyme inhibitors/receptor blockers prescriptions after hospital discharge for heart failure are associated with decreased mortality in Alberta, Canada. J Am Coll Cardiol 2003; 42: 1438-1445].

Improved treatments of heart failure (acute or chronic) and of myocardial infraction are sought for. It is therefore an object of the present invention to provide an improved treatment of myocardial infarction and of heart failure in order to reduce severity and mortality of the diseases. It is furthermore an object of the present invention to provide for an improved therapy of heart insufficiency.

The object of the present invention is, in one particular aspect thereof, solved by the use of Megace® or a pharmaceutically acceptable salt thereof, optionally with appropriate adjuvants and additives for the therapy of improvement of heart function after myocardial infarction and in heart failure. Furthermore, the object of the present invention is solved by the use of Megace® or a pharmaceutically acceptable salt thereof, optionally with appropriate adjuvants and additives for the production of a medicament for the therapy of cardial cachexia and/or heart insufficiency, in particular following myocardial infarction.

In the literature there is no claim or evidence that Megace® is useful in the treatment of myocardial infarction or heart failure.

Based on an animal model, the influence of the appetite stimulant Megace® in heart failure after a myocardial infarction was therefore analysed. For this, the following factors were particularly taken into account:
1. Mortality
2. Infarction size and cardial function
3. Organ weight in comparison Surprisingly, it could be found during these experiments, that Megace® did not have an effect on cardiac cachexia per se (it did not increase body weight), but it improved cardiac function as reflected in improved heart weights and LVEF values as well as survival. This effect was particularly (and thus preferably) present when the microcrystalline novel form of Megace®, i.e. the advanced formulation of megestrol acetate oral suspension (Megace® ES) was used. In order to obtain valid weight measurements, a diuretic was furthermore administered to all animals of the Megace®-study. The use of diuretics is a routine measure in patients with heart insufficiency.

Megace® useable according to the present invention can be provided in any number of forms suitable for administration. Suitable pharmaceutically acceptable forms comprise salts or pre or pro-forms of Megace®.

Examples of pharmaceutically acceptable salts comprise without limitation non toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfate derived from p-toluene-sulfonic acid and others. Such salts can be produced by methods known to someone of skill in the art and described in the prior art.

Other salts like oxalate derived from oxalic acid, which is not considered as pharmaceutically acceptable can be appropriate as intermediates for the production of Megace® or a pharmaceutically acceptable salt thereof.

Megace® or a pharmaceutically acceptable salt thereof can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if Megace® or a pharmaceutically acceptable salt thereof is introduced in finely dispersed, dispersed and suspended form, respectively, or as a suspension of crystals in the medicament or based on the "single unit principle" if Megace® or a pharmaceutically acceptable salt thereof is enclosed in a formulation, e.g. in a tablet or a rod which is subsequently implanted. These implants or depot medicaments in single unit and multiple unit formulations often consist out of so called biodegradable polymers like e.g. polyesters of lactic and glycolic acid, polyether urethanes, polyamino acids, poly(meth)acrylates or polysaccharides.

Adjuvants and carriers added during the production of the medicaments usable according to the present invention formulated as parenterals are preferably aqua sterilisata (sterilised water), pH value influencing substances like, e.g. organic or inorganic acids or bases as well as salts thereof, buffering substances for adjusting pH values, substances for isotonisation like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilisers like e.g. EDTA.

When formulating the medicaments usable according to the present invention as suspensions in a preferred embodiment thickening agents to prevent the setting of Megace® or a pharmaceutically acceptable salt thereof, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrol, carboxymethyl cellulose, Pluronics® or polyethylene glycol sorbit fatty acid ester. Megace® or a pharmaceutically acceptable salt thereof can also be incorporated in liquid formulations in the form of inclusion compounds e.g. with cyclodextrins. In particular embodiments dispersing agents can be added as further adjuvants. For the production of lyophilisates scaffolding agents like mannite, dextran, sucrose, human albumin, lactose, PVP or varieties of gelatine can be used.

In as far as Megace® is not included in a liquid drug formulation in its basic form it can be employed within the parenterals in the form of its acid addition salt solvates.

A further important systemic application formulation is peroral administration in the form of tablets, hard or soft gelatine capsules, coated tablets, powders, pellets, microcapsules, compressed oblongs, granulates, cachets, lozenges, chewing gum or sachets. These solid perorally administered formulations can also be formulated as retard and depot systems, respectively. Comprised therein are medicaments with a content of one or more micronised active agents, diffusion and erosion forms based on matrix, e.g. by using fats, waxy or polymeric substances or so called reservoir systems. If the medicament is formulated to release Megace® over a prolonged period of time retarding agents and agents for the controlled release, respectively, can be added like film or matrix forming substances, for example, ethylcellulose, hydroxypropyl methyl cellulose, poly(meth)acrylate derivatives, (e.g. Eurdragit®), hydroxypropyl-methylcellulose phthalate both in organic solutions and in the form of aqueous dispersions. In this context bioadhesive preparations should also be mentioned wherein an extended dwelling time in the body is caused by the intimate contact with the mucous membranes of the body. An example of a bioadhesive polymer is, e.g. the group of Carbomere®.

For the purpose of a controlled release of Megace® or a pharmaceutically acceptable salt thereof within the different segments of the gastro-intestinal tract it is possible to employ a mixture of pellets which release at different locations. The medicament formulation can be coated, for example, with mixtures of films, substances, compounds or compositions soluble in gastric juice and resistant to gastric juice, respectively. The same purpose of affecting the release in different sections of the gastro-intestinal tract can also be reached with appropriately produced coated tablets with a core, wherein the coating releases the active ingredient in gastric juice rapidly and the core releases the active ingredient in the environment of the small intestine. The aim of a controlled release in different sections of the gastro-intestinal tract can also be achieved by multiple coated tablets. Mixtures of pellets with differentially releasable active agent can be filled into, for example, hard gelatine capsules.

A further adjuvant employed in the production of compressed formulations like e.g. tablets, hard and soft gelatine capsules as well as coated tablets and granules are, for example, counter glue agents, lubricating agents and separating agents, dispersion agents like e.g. flame dispersion silicon dioxide, disintegrants like, e.g. various types of starch, PVP, cellulose, ester as granulating or retarding agent like, e.g. waxy and/or polymeric substances based on Eudragit®, cellulose or Cremophor®.

Furthermore medicaments formulated for peroral administration can comprise antioxidants, sweetening agents like, e.g. saccharose, xylite or mannite, taste correcting agents, flavorants, preservatives, colouring agents, buffering agents, direct compression excipients, microcrystalline cellulose, starch, hydrolysed starch (e.g. Celutab®), lactose, polyethylene glycol, polyvinylpyrrolidone, dicalcium phosphate, lubricants, fillers like, e.g. lactose or starch, binders in the form of lactose, types of starch like e.g. wheat or corn and rice starch, respectively, derivatives of cellulose like, e.g. methyl cellulose, hydroxypropyl cellulose or silica, talcum, stearate like, e.g. magnesium stearate, calcium stearate, talkum, siliconised talkum, stearic acid, cetyl alcohol or hydrogenated fats etc. A variety of substances are known to someone of skill in the art which can be added to medicaments for the formulation for peroral administration.

In a further embodiment Megace® or a therapeutically acceptable salt thereof can also be formulated as an oral therapeutic system, in particular based on osmotic principles like, e.g. GIT (gastro-intestinal therapeutic system) or OROS (oral osmotic system).

Effervescent tablets or tabs are also among compressed formulations, which can be perorally administered and which are both rapidly dissolvable or suspendable in water and are rapidly drinkable instant drug formulations.

Perorally administrated formulations also include solutions e.g. drops, juices and suspension which can be produced according to methods known in the art and which can comprise—beside the already mentioned adjuvants and additives for the increase of the stability—preservatives and if desired flavouring agents for easier ingestion and colouring agents for better distinction as well as antioxidants and/or vitamins and sweetening agents like sugars or artificial sweeteners. This also applies to dried juices which are prepared with water prior to use. In a preferred embodiment of a formulation of the medicaments of the present invention an ingestible liquid formulation can also comprise an ion exchange resin.

In a preferred embodiment of the present invention, the Megace® is selected from common Megace® and/or novel Megace®. As an example, Megace® is commercially produced by several companies as generic medicament. For the present study, two forms of Megace® were used that were obtained from the company PAR Pharmaceuticals (see above).

In yet another preferred embodiment of the present invention, the CHI is based on coronary heart disease.

Yet another preferred embodiment of the present invention is characterised in that the medicament is applied orally. Preferably, Megace® or a pharmaceutical acceptable salt thereof is applied in a dosage of between 30 mg/d and 2000 mg/d, preferably between 100 mg/d and 1600 mg/d, most preferred 300 to 800 mg/d. The active ingredient can be administered in one or several doses per day; alternatively the active ingredient can be administered in larger time intervals. Also preferably, Megace® or a pharmaceutical acceptable salt thereof is applied in a dosage of between 4 and 15 mg/kg/d. The active ingredient can be administered in one or several doses per day; alternatively the active ingredient can be administered in larger time intervals.

In another important embodiment of the present invention, Megace® or a pharmaceutical acceptable salt thereof is applied in combination with drugs typically used in CHI, such as suitable diuretics, vasodilators, digitalis, an ACE-inhibitor, an angiotensin-II receptor antagonist, a beta-blocker, an aldosterone antagonist, an endothelin receptor antagonist, a xanthin oxidase inhibitor, a statin (a HMG-CoA reductase inhibitor) and/or bile-acid resins (such as cholestyramine (Questran®) and colestipol (Colestid®)), cholesterol absorption inhibitors (such as Ezetimibe (Zetia®), nicotinic acid (niacin), and fibric acid derivatives (fibrates), such as fenofibrate (TriCor®) and gemfibrozil (Lopid®). Preferably, the diuretic is furosemide.

The invention also relates to a composition comprising Megace® or a pharmaceutical acceptably salt thereof in combination with a suitable diuretic, a vasodilator, digitalis, an ACE-blocker, and/or a beta-blocker. Preferably, the diuretic is furosemide.

The compositions according to the present invention comprising one or more suitable diuretic, a vasodilator, digitalis, an ACE-blocker, and/or a beta-blocker can be produced by someone of skill in the art in one of the formulations disclosed above for Megace® and can be mixed with respectively indicated adjuvants and additives. In a further aspect the invention also relates to the spatially and/or temporally separated administration of the respective active ingredients.

It was a main goal of the study underlying the present invention as well as other studies, to reach a reduced mortality in addition to an increase of weight and a better stability of the patient's weight. Since in most patients having chronic heart insufficiency oedema occur, nearly all human patients with heart insufficiency are undergoing a therapy with a diuretic [Cowie M R, Mosterd A, Wood D A, Deckers J W, Poole-Wilson P A, Sutton G C, et al. The epidemiology of heart failure. Eur Heart J 1997; 18:208-225]. Prior studies have shown that also in diseased rats, that are used as a model in present invention, oedema occur which would interfere with the measurements of weight and the comparisons. Thus, all infarct animals were given furosemide together with drinking water. It can therefore be expected that the changes in weight are with a high probability related to an increase or decrease of fat, muscle or bone mass and are not caused by oedema. In addition, the results as indicated in Example 2, below, show that furosemide has no effect on the echocardiographically determined heart function.

In an infarct model sub-acute infarctions having a chronic progress develop. The generation of a CHI in human in any cases is caused by a myocardial infarct. Thus, the infarct model allows for representative results for chronic heart insufficiency. In the present invention, the red infarct model for the production of a chronic heart insufficiency was therefore used.

In another aspect of the present invention, furosemide was used together with Megace® in order to provide for a further improved combination therapy.

Another aspect of the present invention is related to a method for improving cardic function and/or the treatment of chronic heart insufficiency in a mammal, comprising providing an effective amount of megestrol acetate or a pharmaceutically acceptable salt thereof to said mammal, optionally with suitable adjuvants and additives, as already explained above. Preferably, said mammal is a human. More preferably, said megestrol acetate is selected from common megestrol acetate oral suspension (Megace®) and/or Megace® ES.

According to said method according to the present invention, said chronic heart insufficiency can result from a cardiomyopathy, in particular chronic heart insufficiency resulting from a cardiomyopathy due to myocardial infarction.

Preferably, said effective amount of megestrol acetate or pharmaceutically acceptable salt thereof is applied orally. More preferably, said megestrol acetate or a pharmaceutical acceptable salt thereof is applied in a dosage of between 30 mg/d and 2000 mg/d, preferably between 100 mg/d and 1600 mg/d, most preferred 300 to 800 mg/d. More preferably, said megestrol acetate or a pharmaceutical acceptable salt thereof is applied in a dosage of between 4 and 15 mg/kg/d.

Another aspect of the present invention is related to a method according to the present invention, wherein said megestrol acetate or a pharmaceutical acceptable salt thereof is applied in combination with drugs typically used in CHI, like a suitable diuretic, a vasodilator, digitalis, an ACE-inhibitor, an angiotensin-II receptor antagonist, a beta-blocker, an aldosterone antagonist, endothelin receptor antagonist, a xanthin oxidase inhibitor, a statin (a HMG-CoA reductase inhibitor) and/or bile-acid resins, cholesterol absorption inhibitors, nicotinic acid, and fibric acid derivatives. Preferably said diuretic is furosemide.

The following conclusions can be drawn from the present experiments. The myocardial infarction induced in rats nearly always leads to a proven heart failure in these rats. Rats having an surgically induced myocardial infarction have a lower chance of survival compared to sham-surgery rats. Novel megestrol acetate significantly improved the heart function parameters LVEF and FS in infarction surgery rats in comparison to placebo. Novel megestrol acetate significantly improved the survival in infarction surgery rats in comparison to placebo.

The following examples and figures are included to demonstrate preferred embodiments of the invention. It should be appreciated by those of skill in the art that the techniques disclosed in the examples that follow represent techniques discovered by the inventors to function well in the practice of the invention, and thus can be considered preferred modes for its practice. However, those of skill in the art should, in light of the present disclosure, appreciate that many changes can be made in the specific embodiments that are disclosed without departing from the spirit and scope of the invention as set out in the appended claims. For the purposes of the present invention, all references as cited are incorporated herein by reference in their entireties.

FIGURES

In FIG. 1, the development of weight for all groups is depicted.

In FIG. 2, the mean changes of weight in the infarction-groups placebo, old and novel megestrol acetate together with the standard deviation are depicted. All infarction-surgery groups received furosemide. For comparison, the sham-surgery group is depicted that did not receive furosemide.

In FIG. 3, the changes of weight in the infarction-groups following the end of therapy together with the standard deviation are depicted. All groups received furosemide.

Figure 9:
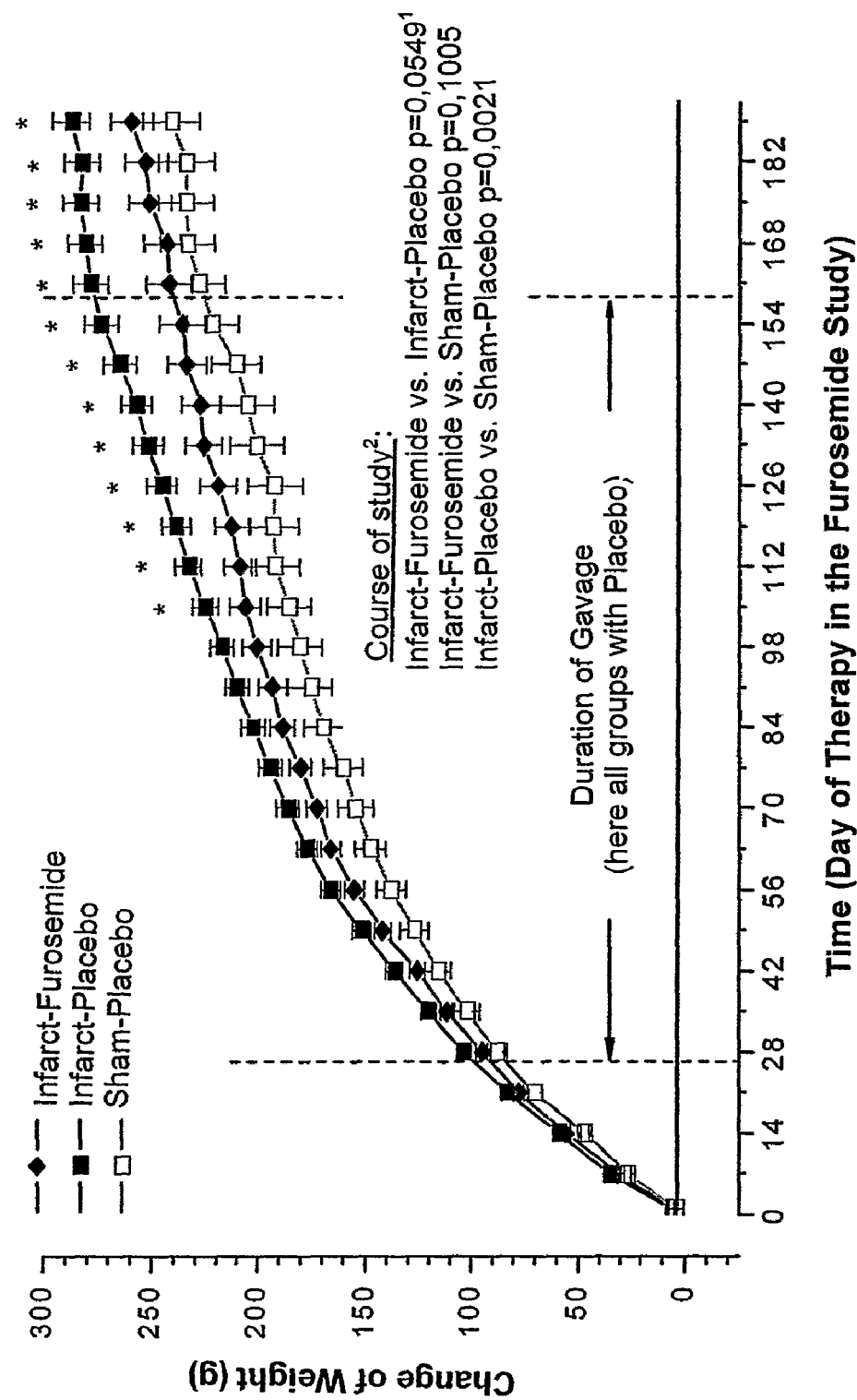

FIG. 9 shows the mean change of weight with standard deviation. All depicted groups received placebo in the gavage. [1]A significance (indicated by * for p<0.05) can be found starting from day 105 for infarction-furosemide vs. infarction-placebo. [2]The analysis only contained animals that survived until the end of the study: infarction-furosemide: 23 of 39, infarction-placebo 30 of 33, sham-placebo 12 of 12.

EXAMPLES

Briefly, two animal studies were performed, wherein in the first study a ligation of the left coronary artery was performed in 280 animals. Infarct size was 32±1% and 24 hour mortality was 40%, both indicating large infarcts. After two weeks, rats were started on a diuretic (furosemide, 8.6 mg per 100 ml drinking water). After six weeks, double-blind randomised therapy with one of the two forms of MA or placebo was started and continued for 18 weeks. After the end of the therapy, rats were followed for a further 6 weeks. Then, animals were studied for cardial function (echocardiography) and thereafter sacrificed.

In the first study, neither form of MA increased body weight; rather it was found to be significantly lower in MA treated animals (p<0.001). Subjectively, the research fellow involved reported that the rats treated with new MA were more active.

Survival: Rats with new MA had a 55% lower mortality than rats receiving placebo (new MA vs. placebo: Hazard Ratio 0.45, confidence interval [CI] 0.15-1.32. p=0.13). This effect was not found for old MA (old Megace® vs. placebo: Hazard Ratio 0.79, p=0.63).

Cardiac function and weight: Both old and new MA reduced the left ventricular mass (p<0.05 vs. placebo). Only new MA improved cardiac function significantly, as assessed by echocardiography left ventricular ejection fraction [LVEF] (41±2 vs. 35.5±2%, p=0.04 vs. placebo) and fractional shortening [FS] (17.9±1 vs. 15.1±1%, p=0.04 vs. placebo). This was not statistically significant with old MA (mean LVEF 39±2% and FS16.8±1%: vs. placebo: p=0.23 and p=0.21, respectively).

This study showed surprising results, in that old and new Megestrol acetate did not increase body weight. The new Megestrol acetate appears to have effects that contributed to significant improvements in cardiac function and a strong trend towards better survival.

A second study was performed using the same methodology as in the first study. Again ligation of the left coronary artery in rats was performed with diuretic therapy starting at 2 weeks and treatment with MA starting after 6 weeks. In 4 groups (all treated with a diuretic), animals received either placebo (number of animals: n=38), old (n=37) or new MA (n=40) or an ACE inhibitor (Ramipril®, n=38).

Survival in study 2: After a mean follow up of 15 weeks, the following number of dead animals per group was found: new MA: 1 (=2.5%); old MA: 17 (=45.9%); Placebo: 16 (=42.1%); ACE inhibitor: 2 (=5.3%). These results reached significance for new MA vs. placebo and vs. old MA (both p<0.01).

This study confirmed that new Megestrol acetate improves survival in rats after a myocardial infarction.

Animals

Male Wistar-rats (Dimed GmbH, Schönwalde, Germany) were held in an environment controlled animal facility having a constant temperature of 23° C. in a 12 hour day-night-cycle.

During the whole experiment, all rats were grouped in 1-3 animals per cage. Animals in one cage belong to the same group. The animals had free access to regular food and drinking water or drinking water with diuretic respectively.

Production of a Heart Insufficiency Via Infarction Surgery 280 animals underwent surgical treatment at a weight of about 215-230 g (221±1 g). In order to produce a heart insufficiency the inventors performed the surgical treatment in accordance with an infarction model that was already used in several prior studies. The heart infarction is produced according to a slightly modified method described by Selye et al. [Selye H, Bajusz E, Grassos S, Mendel P. Simple techniques for the surgical occlusion of coronary vessels in the rat. Angiology 1960; 11: 398-407] by ligation of the LAD.

Each rat is anaesthetised by i.p. chloralhydrate (Merck, Darmstadt, Germany) and is subsequently intubated with a PE-catheter (1.2 mm diameter) and respired using a Rodent-respirator UB 7025-10 (Föhr Medical Instruments GmbH, Seeheim/OB, Germany). The thorax was opened, the heart was prepared and a ligature using Ethibond-suture material 7/0 (Ethicon GmbH, Norderstedt, Germany) was made in position of the left coronary artery (LAD). Since the coronary arteries during this process can not be viewed by the naked eye, the orientation occurred anatomically based on the position of the heart and the visible coronary veins. The success of the infarction could be visually verified based on the occurring paleness, cyanosis and mobility distortion. Subsequently, the thorax was closed. The respiration was ended, once a stable ECG was reached. 41 rats were used as control animals and were surgically treated in the same manner as the infarction animals. No coronary ligature was introduced in these animals (sham-surgery).

After the surgery, the animals were controlled and the weight was analysed twice a week during the whole study. 18 days (between day 16-20) post-surgery the animals were randomised and segregated into the respective groups. After this point in time, the respective groups received furosemide until the end of the study. After an additional four weeks, the daily gavage was started. This was maintained for 18 weeks and subsequently stopped. In the following observation period, the animals were controlled. Echocardiography was performed and the weight was controlled.

Randomisation and Blinding 14 days post-surgery, all infarction and control animals were block-randomised and segregated in one of four infarction groups or one of three control groups. The groups were designated as follows: infarction-placebo (without furosemide), infarction-A, infarction-B, infarction-C, sham-A, sham-B, sham-C. For the medicaments A, B and C all persons participating in the study were blinded (double-blind controlled trial). One of the medicaments A, B or C was a placebo (with furosemide), therefore the corresponding group was the comparative group for both studies (Megace® and furosemide-study, respectively).

Weight Determinations

During the progression of both studies, the animals were weight-determined twice a week, starting from the date of surgery (laboratory balance model CS2000. Ohaus Corporation, Pine Brook, N.J., USA). The results were calculated corresponding to the post-surgical day of the respective animal.

Diuretic Treatment

Groups A, B and C of the infarction animals received furosemide (Lasix® 250 mg ampoule, Aventis Pharma GmbH, Frankfurt am Main, Germany) starting from day 18 (±2 days) for the whole study in a concentration of 8.6 mg/100 ml in drinking water. This corresponds to an initial dosage of 10 mg/kg/d at a weight of 300 g and an amount of drinking water of 35 ml/d.

Animals from the infarction-placebo group (without furosemide) and all sham-animals received drinking water without supplementation.

Medication

Megestrol acetate or control substances were administered to the animals via gavage. Depending on the time of surgery, the animals were gavaged starting from week six (day 44±2) until week 24 after the infarction surgery once a day, whereby the amount of gavage was adjusted to the weight (100 mg old Megace®/kg body weight per day, 1 ml solution contains 40 mg old or new Megace® or placebo, respectively).

For the infarction-placebo without diuretic, a further placebo-solution (non-blinded) was produced consisting of 0.2% sodium benzoate (ICN Biomedicals GmbH, Eschwege, Germany), dissolved in drinking water. This corresponded to the solvent of substances A, B and C. Corresponding to the respective groups, the infarction animals received the placebo-solution or the substance A, B or C and the control animals merely substance A, B or C. Substances were mixed on a magnetic stirrer (Cycler, Typ RCT basic, IKA Labortechnik, Stauten, Germany).

TABLE 1

Gavage protocol. 1 ml of the solution contained 40 mg of old or new megestrol acetate or placebo, respectively.

| Animal weight (g) | Gavage (amount) |
| --- | --- |
| 180-219 | 0.5 ml |
| 220-259 | 0.6 ml |
| 260-299 | 0.7 ml |
| 300-339 | 0.8 ml |
| 340-379 | 0.9 ml |
| 380-419 | 1.0 ml |
| 420-459 | 1.1 ml |
| 460-499 | 1.2 ml |
| 500-539 | 1.3 ml |
| 540-579 | 1.4 ml |
| 580-619 | 1.5 ml |
| 620-659 | 1.6 ml |
| 660-699 | 1.7 ml |
| 700-739 | 1.8 ml |
| 740-779 | 1.9 ml |
| 780-819 | 2.0 ml |

Follow-Up Observations

Starting from week 24 to week 30 post-surgery, the animals were subjected to follow-up controls, i.e. the gavage was ended (substances A, B and C of the Megace® study and the placebo in the diuretic study), the animals were further weight-determined twice weekly and the respective groups further received drinking water containing furosemide. Echocardiography was performed with all animals that were alive at this point of time with 6-8 animals per group, respectively.

Preparation of Organs

In the 31st week post-surgery, the surviving animals were anaesthetised using chloralhydrate lp. 4 mg/kg body weight (Sigma-Aldrich Chemie GmbH, Deisenhofen, Germany). Following the preparation of the subscapular brown fatty tissue, lapratomisation was performed and blood was drawn from the aorta abdominalis into EDTA-flushed 10 ml syringes (Roth, Karlsruhe, Germany) and added to pre-chilled 12 ml-tubes (Sarstedt, Nümbrecht, Germany). The heart was removed, weight-determined, the area of infarction was drawn, separated into atrium, septum, ventriculum, and area of infarction, and the individual pieces were frozen in liquid nitrogen in 2.0 ml Eppendorf-tubes (Fisher, Schwarte, Germany) and stored frozen at −80° C.

The following parts were removed completely or partially: lung, liver, kidneys, renal glands, inguinal fatty tissue, epididymal fatty tissue, jejunum, colon descendens, right quadriceps, and gastrocnemius, brain and eyes.

For histological preparation the parts of the gut were preparated and fixed in Zamboni (15% saturated picrinic acid, 2% formaldehyde) [119]. The muscles were each dissected and one part was frozen in nitrogen and the residue was also fixed in Zamboni. All other organs were frozen in liquid nitrogen and stored at −80° C. The blood was centrifuged for 10 minutes at 4° C. and 3000 rpm in a chilled centrifuge (CL-GPICR, Beckmann, UK), and the plasma was stored at −80° C. in Eppendorf-tubes.

Echocardiography

Figure 1:
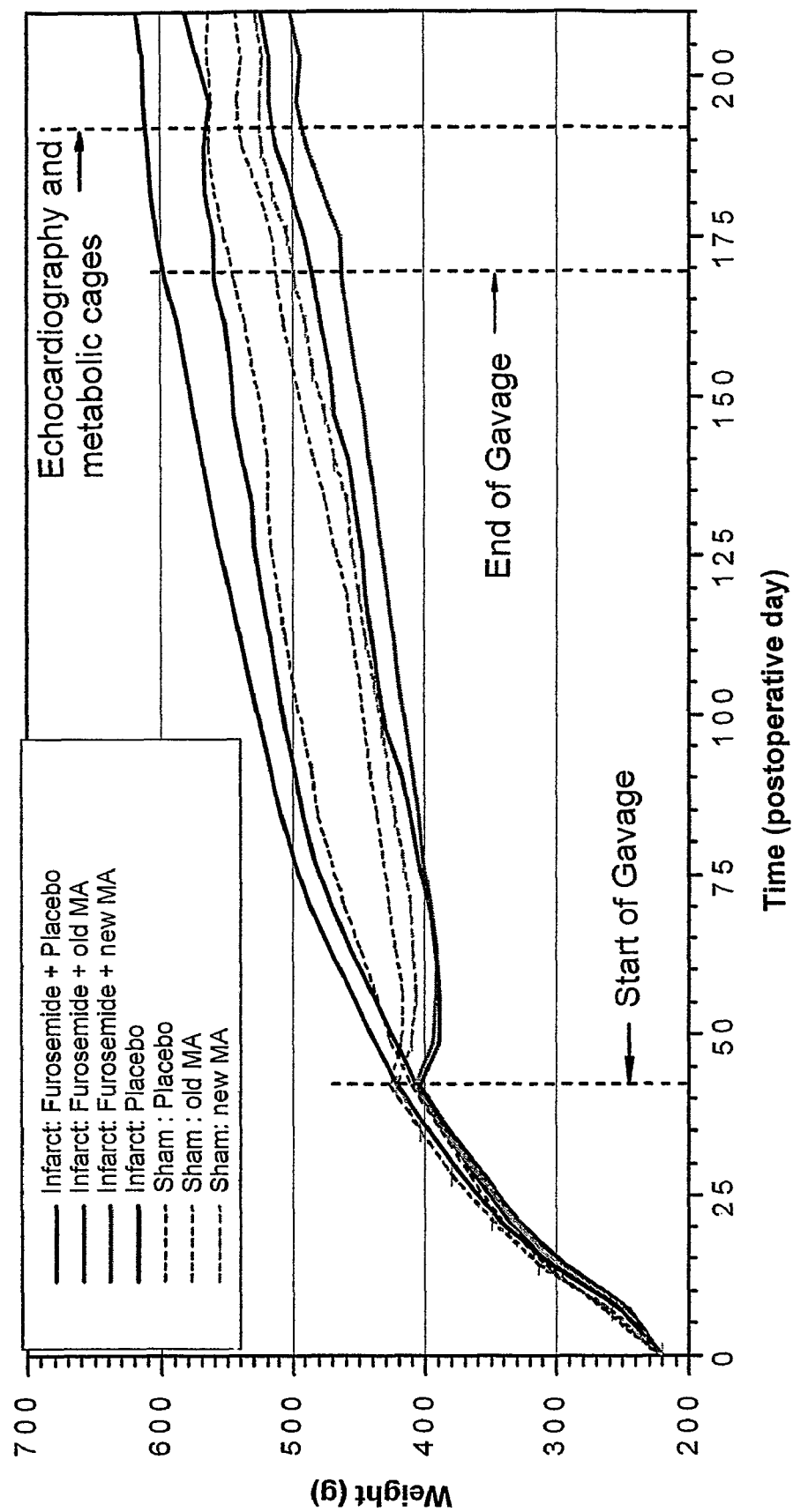

Between week 28 and 30 post surgery (corresponds to week 22 to 24 in the megestrol acetate-Study or week 25 to 27 in the diuretic study), the heart function of all rats still alive was examined by echocardiography. For this, each rat was first pre-anaesthetised using isoflurane (Curamed Pharma GmbH Karlsruhe, Germany) in a chamber of the anaesthetic unit Univentor 400 Anaesthesia Unit (Agn Tho's, Lidingö, Sweden) pre-anaesthetised and subsequently maintained by using a mask. For the echocardiography examination the thorax region was shaved and the rat was fixed in a position lying on the back. The echocardiography was performed with an Acuson-Sequoia C256 (Siemens, Germany) which was equipped with a 15 MHz sonication head suitable for rat- and mouse echocardiography. The left ventricle (LV) was adjusted in the parastemal long and short axis. In the M-mode, the short axis, the systolic and end-diastolic thicknesses of walls (anterior and inferior) and the LV-diameter ware measured and based on the fractional shortening (FS) the left ventricular function, and the left ventricular ejection fraction (LVEF) were determined. The diastolic function was evaluated based on the LV-influx profile via the mitral valve (E/A-ratio) by means of a PW-Doppler. The measurement volume of the PW-doppler was placed at the tip of the opened mitral valve flap. The measurements were performed by an independent blinded researcher. In FIG. 1 the progression of weight for all groups is depicted.

Statistical Analysis

All results were indicated as mean value± standard deviation. In order to determine differences between groups, the unpaired t-test was performed in case of up to two groups, in case of several groups, analyses of variances (ANOVA) and Fisher post hoc were performed. In repeated measurements (weight analysis) the repeated measure ANOVA was used. In non-normally segregated data the Mann-Whitney-Test was used in two groups. For the analysis of survival, the Cox-proportional-Hazard-model was used. The Hazard-ratio and the 95% confidence interval for the risk factors as well as p-values for $\chi 2$ are indicated (Likelihood-Ratio-Test). The Hazard-ratio for the continuous variable relates to the relative risk per unit of the variables as analysed. For depicting the probabilities of survival, Kaplan-Meier-plots were generated. In normally-segregated data, a p-value of <0.05 was regarded as significant. In the box-diagrams, the whiskers indicate the standard deviation. All calculations were performed using the StatView (Version 5.0 for Windows, SAS Institute Inc., Cary, N.C., USA) statistics program.

Example 1

Megestrol Acetate-Study

Progression of Weight in the Infarction Surgery Group

Figure 2:
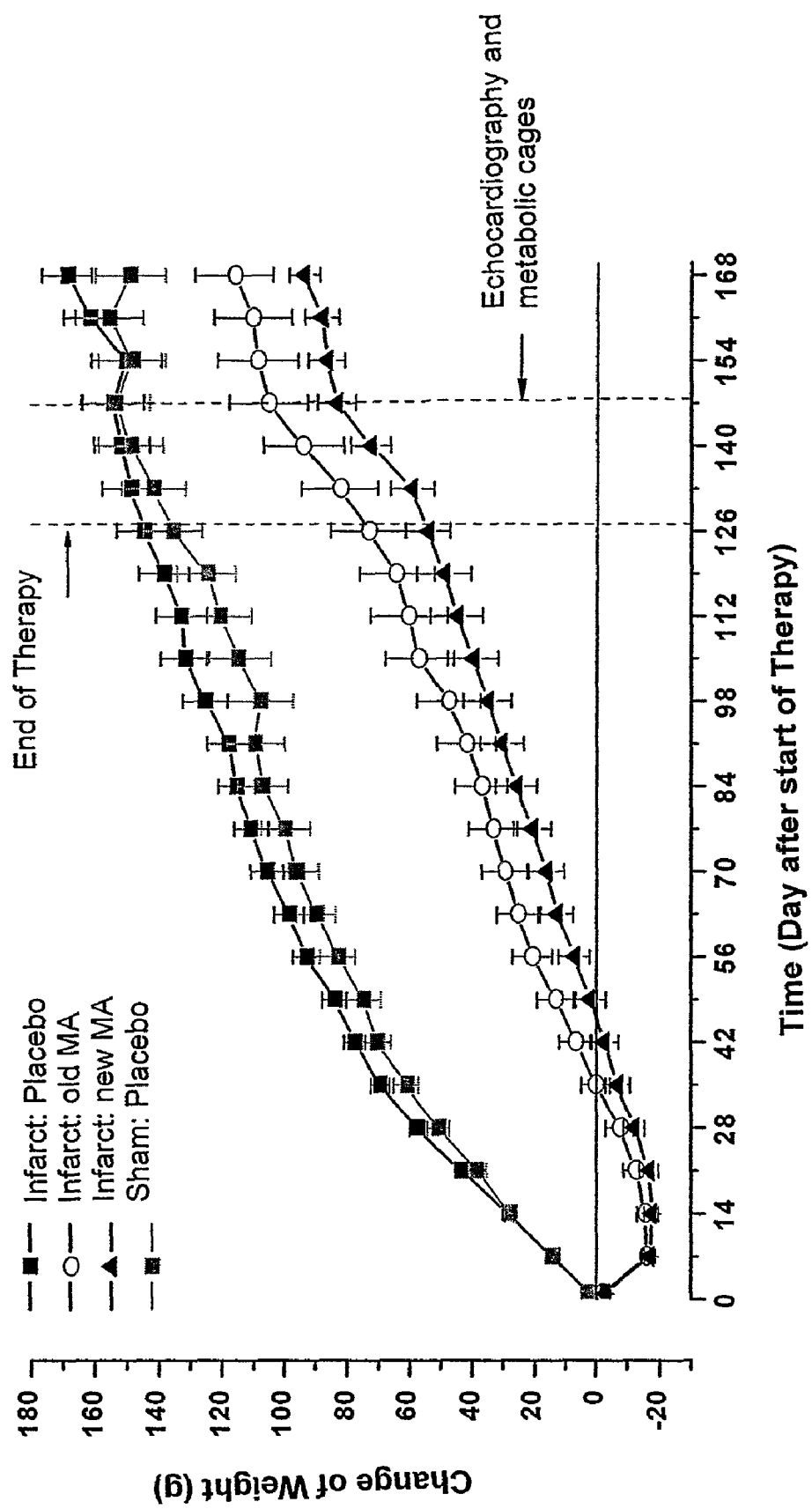

The values of weights were compared corresponding to the day post surgery of the respective animals. Due to the different weights (408±3 g/min. 281 g-max. 485 g) of the test-animals at the beginning of the therapy (day 0), the progression of weight was related to the initial weight of the respective animal at start of therapy. In FIG. 2, the changes in weight of the three infarction-study groups (placebo, old and novel megestrol acetate) are depicted for the whole course of the therapy.

An increase of weight in all three groups was observed throughout the duration of the experiment. The final weights and the course of the increase of weight are very different between the groups. The response of the placebo-group differs significantly from both megestrol acetate groups (infarction-placebo vs. infarction-old megestrol acetate p=0.0002, infarction-placebo vs. infarction-novel megestrol acetate p<0.0001). Both megestrol acetate-groups do not differ significantly (p=0.36).

Whilst an immediate and continuous increase was seen in the placebo-group, for the megestrol acetate groups a weight loss until day 35 (old megestrol acetate) or until day 46 (novel megestrol acetate) was observed. The maximal weight loss after start of the therapy was −15.8±1.5 g (4,0%, n=31) and −17.6±2.3 g (4.4%, n=32) in the animals, who experienced therapy with the old and novel megestrol acetate, respectively. Following day 35 after the beginning of therapy (until the end of therapy), the weight increase for all groups paralleled. The increase of weight per day was +0.8 g/d and +0.7 g/d in the groups with old and novel megestrol acetate and +0.8 g/d in the placebo-groups.

Figure 3:
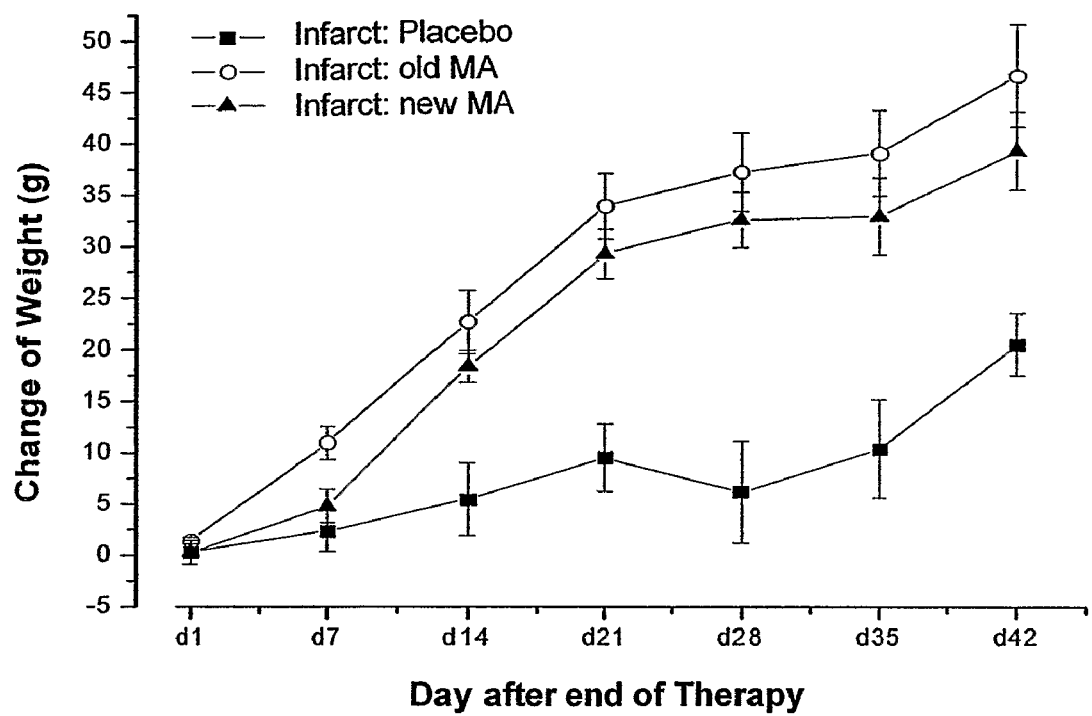

After the end of therapy a significant acceleration of the weight increase was found during the course of 21 days in the animals from both megestrol acetate-groups. In contrast, no change in the weight increase of the placebo-group could be observed (p<0.0001). The changes of weight starting from the end of therapy are separately depicted in FIG. 3.

The increases until day 21 following the end of the therapy were +1.5 g/d and +1.4 g/d for the old or novel megestrol acetate, respectively, but only +0.5 g/d for placebo. Starting from day 21 after the end of therapy until the end of the experiment, the increase of weight in den three groups became nearly equal again (+0.5 g/d in both megestrol acetate-groups and +0.7 g/d in the placebo-groups)

At end of gavage (between day 119-137), the absolute changes of weight since start of therapy in the animals that underwent therapy with megestrol acetate were lower as in the animals that underwent therapy with placebo (old megestrol acetate 73±12 g [n=25], novel megestrol acetate 54±7 g [n=28], placebo 144±8 g [n=27]; p<0.0001). This ratio continued until the end of the observation period (day 167 to 179), the mean values in the groups were 169±8 g, [n=23] for placebo, 116±12 g, [n=24] for old megestrol acetate and 93±5 g, [n=28] for the novel megestrol acetate. Both megestrol acetate-groups exhibited significant differences vs. placebo for this day (both p<0.0001), but not compared to each other (p=0.06). An overview of the weight of the animals based on selected test animals is given in the following table 2.

TABLE 2 mean absolute weights with standard deviation of the study-groups in the megestrol acetate-study at the beginning of therapy (day 0), end of therapy (day 126) and end of follow-up (day 168), A significance of p < 0.0001 vs. placebo is indicated by ***. All groups received furosemide.

| Time (day) | Infarction Placebo weight (g) | n | Infarction old MA weight (g) | n | Infarction novel MA weight (g) | n |
|---|---|---|---|---|---|---|
| 0 | 411 ± 5 | 33 | 404 ± 8 | 32 | 408 ± 4 | 32 |
| 126 | 559 ± 12 | 27 | 485 ± 17*** | 25 | 462 ± 10*** | 28 |
| 168 | 582 ± 12 | 23 | 525 ± 16*** | 24 | 502 ± 8*** | 27 |

The comparison over the complete observation period from the beginning of the therapy with megestrol acetate shows a significant difference between the groups (repeated measures ANOVA). The weight increase in the animals that received the placebo per gavage was significantly higher as in both groups that were treated with megestrol acetate ($p<0.0001$). In total, the difference between the megestrol acetate-groups was not statistically significant ($p=0.14$).

Echocardiography

The echocardiography examination was performed in all alive animals and was used for a determination of the anatomic situations and the function of the heart. In addition to the evaluation of functional parameters, primarily the size relations of the heart cavities and the heart wall thicknesses can be estimated, whereby functional parameter such as the LVEF and the FS should allow for a statement with respect to the myocardial contractility. The function of heart valves was not examined.

TABLE 3

Echocardiography parameters for the infarction-surgery groups of the megestrol acetate-study. The infarction-surgery groups all received furosemide.

|  | Infarction-Placebo n = 20 | Infarction-old MA n = 23 | Infarction-novel MA n = 26 |
|---|---|---|---|
| LVEDD (cm) | 1.06 ± 0.02 | 1.04 ± 0.03 | 1.03 ± 0.02 |
| LVESD (cm) | 0.90 ± 0.02 | 0.87 ± 0.03 | 0.85 ± 0.02 |
| LVHW d (cm) | 0.17 ± 0.01 | 0.17 ± 0.01 | 0.17 ± 0.004 |
| IVS d (cm) | 0.13 ± 0.03 | 0.14 ± 0.04 | 0.10 ± 0.002 |
| FS (%) | 15.1 ± 0.9 | 16.8 ± 0.9 | 17.9 ± 0.9* |
| LVEF (%) | 35.5 ± 2.0 | 39.0 ± 1.8 | 41.0 ± 1.8* |
| E (m/s) | 0.84 ± 0.03 | 0.82 ± 0.03 | 0.80 ± 0.03 |
| A (m/s) | 0.62 ± 0.05 | 0.55 ± 0.05 | 0.57 ± 0.04 |
| E:A | 1.61 ± 0.21 | 1.85 ± 0.23 | 1.56 ± 0.11 |

LVEDD: left ventricular end-diastolic diameter,
LVESD: left ventricular end-systolic diameter,
LVHW: left ventricular back wall,
IVS: inter-ventricular septum,
d: end-diastolic measurement,
FS: fractional shortening (left ventricular),
LVEF: left ventricular ejection fraction,
E:A: effect profile over the mitral valve.
*$p < 0.05$ vs. placebo.

TABLE 4

Echocardiography parameters in the sham-surgery groups (without furosemide).

|  | Sham-placebo n = 11 | Sham-old MA n = 12 | Sham-novel MA n = 12 |
|---|---|---|---|
| LVEDD (cm) | 0.82 ± 0.02 | 0.87 ± 0.03 | 0.83 ± 0.03 |
| LVESD (cm) | 0.49 ± 0.04 | 0.55 ± 0.04 | 0.51 ± 0.05 |
| LVHW d (cm) | 0.17 ± 0.01 | 0.14 ± 0.01 | 0.17 ± 0.01 |
| IVS d (cm) | 0.26 ± 0.02 | 0.25 ± 0.02 | 0.28 ± 0.02 |
| FS (%) | 41.1 ± 3.0 | 38.0 ± 3.0 | 39.3 ± 3.2 |
| LVEF (%) | 75.8 ± 4.0 | 71.8 ± 4.1 | 73.1 ± 4.4 |
| E (m/s) | 0.78 ± 0.04 | 0.78 ± 0.04 | 0.78 ± 0.04 |
| A (m/s) | 0.60 ± 0.05 | 0.66 ± 0.03 | 0.71 ± 0.04 |
| E:A | 1.39 ± 0.16 | 1.18 ± 0.06 | 1.16 ± 0.05 |

Systolic and Diastolic Diameter of the Ventricle

The diameter of the left ventricle were determined systolically and diastolically in the M-mode. The infarction-groups (placebo vs. megestrol acetate) do not differ significantly from each other (see table 3). All infarction-groups together nevertheless show systolic and diastolic significantly larger diameters ($p<0.0001$) compared to the sham-surgery groups (see table 5). The sham-surgery groups did not differ between each other in all echocardiography values (see table 4).

Thickness of Posterior Wall and Ventricular Septum

In order to elucidate a ventricular hypertrophy, the thicknesses of the interventricular septum (IVS) and the left ventricular posterior wall (LVHW) were diastolically determined. The values show that no hypertrophy is present in the area of the septum (see table). Nevertheless, the posterior wall is significantly thicker in all infarction-groups, compared to the sham-surgery animals ($p=0.02$, see table 5). Between the infarction-groups there is no difference (see table).

TABLE 5

Echocardiography parameters for the infarction- and sham-surgery groups of the megestrol acetate-study. The infarction-surgery groups received furosemide, the m-surgery groups did not receive furosemide.

|  | Infarction-Surgery n = 69 | Sham-Surgery n = 34 | p-Value |
|---|---|---|---|
| LVEDD (cm) | 1.04 ± 0.01 | 0.84 ± 0.02 | <0.0001 |
| LVESD (cm) | 0.87 ± 0.01 | 0.52 ± 0.02 | <0.0001 |
| LVHW d (cm) | 0.17 ± 0.003 | 0.16 ± 0.004 | 0.02 |
| IVS d (cm) | 0.12 ± 0.01 | 0.14 ± 0.003 | 0.39 |
| FS (%) | 16.7 ± 0.5 | 39.3 ± 1.7 | <0.0001 |
| LVEF (%) | 38.8 ± 1.1 | 73.4 ± 2.4 | <0.0001 |
| E (m/s) | 0.82 ± 0.01 | 0.78 ± 0.02 | 0.19 |
| A (m/s) | 0.58 ± 0.03 | 0.66 ± 0.03 | 0.05 |
| E:A | 1.67 ± 0.10 | 1.23 ± 0.05 | 0.01 |

LVEDD: left ventricular end-diastolic diameter,
LVESD: left ventricular end-systolic diameter,
LVHW: left ventricular back wall,
IVS: inter-ventricular septum,
d: end-diastolic measurement,
FS: fractional shortening (left ventricular),
LVEF: left ventricular ejection fraction,
E:A: effect profile over the mitral valve.

Left Ventricular Ejection Fraction and Fractional Shortening

In order to have a measure for the global myocardial contraction (pumping function of the left ventricle) the fractional shortening (FS) based on the left ventricular end-diastolic and end-systolic diameter, and for a determination of the ejection volume the left ventricular ejection fraction (left ventricular ejection fraction, LVEF) was calculated.

Generally, the LVEF was significantly reduced in the infarction animals vs. the sham-surgery animals (see table 5, $p<0.0001$). The analysis of the LVEF resulted in an improved LVEF of novel megestrol acetate vs. placebo ($p=0.04$), the group with old megestrol acetate did not differ from the placebo-groups ($p=0.21$), see table 3. The LVEF that was improved by 5.5% (absolute value, relative 15.5%) in the group with the novel megestrol acetate results in ANOVA in a significant difference vs. the placebo-group.

Figure 4:
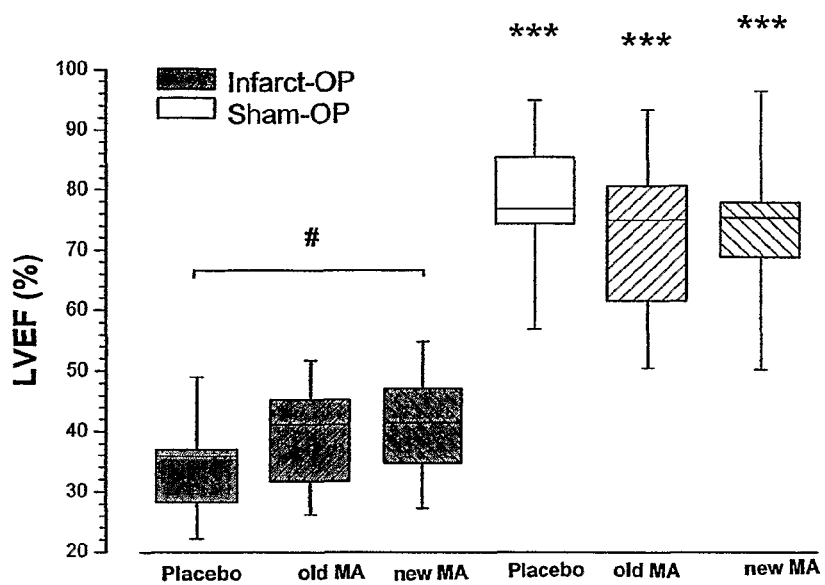
FIG. 4 shows the ejection fraction of the left ventricle in the infarction-groups and the sham-surgery groups in the megestrol acetate-study. ***p<0.001 vs. the corresponding infarction-group, # p<0.05 vs. infarction-placebo.
Figure 5:
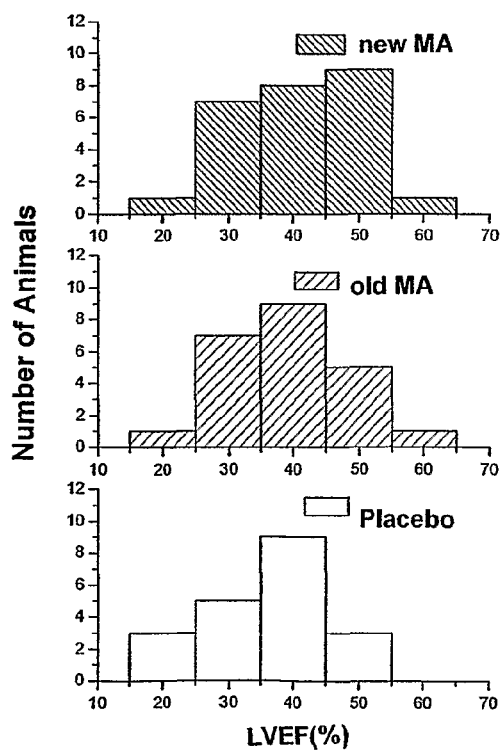
FIG. 5 shows the normal segregation of the LVEF in the infarction-groups. The Kolmogorov-Smirnov-test leads to p<0.05.

At the analysis of the shortening fraction (FS) showed a nearly identical behaviour as for the ejection fractions. The infarction-groups show lower FS-values compared to the sham-surgery animals ($p<0.0001$), see table 5. Old megestrol acetate did not differ from the placebo-group ($p=0.23$), see table 3. Novel megestrol acetate results in an absolute 2.7% (relative 18.0%) higher and thus better shortening fraction vs. the placebo-group ($p=0.04$). FIG. 4 shows the ejection fraction of the left ventricle in the infarction-groups and the sham-surgery groups in the megestrol acetate-study. ***$p<0.001$ vs. the corresponding infarction-group, #$p<0.05$ vs. infarction-placebo, FIG. 5 shows the normal segregation of the LVEF in the infarction-groups. The Kolmogorov-Smirnov-test leads to $p<0.05$.

Diastolic Function

For determining the diastolic function the early-(E) and late-diastolic (A) blood flow from the left atrium into the ventricle was measured using doppler-sonography. The ratio of E to A (E/A-Ratio) is regarded as a measure for the early diastolic relaxation of the myocardium. The value did not result in significant differences between the groups. The general comparison between the infarction- and sham-surgery groups (see table 5) results in a significantly lower and therefore improved value for the sham-surgery animals (p=0.005).

In summary, the measurement show a worsened heart function of the infarction-animals in comparison with the sham-animals. In the individual infarction-groups novel megestrol acetate improved the LVEF by 15.5% and the FS by 18.0% vs. the placebo-group (p=0.04 each).

Organ Weights

In all alive animals, certain organs were removed for further analysis. At identical variance with respect to the size of infarction a significantly reduced heart weight could be found in those animals that underwent therapy using the novel megestrol acetate, i.e. the cardial hypertrophy was lower (see table 7). Furthermore, the weight of the lungs in the group with the novel megestrol acetate was significantly lower vs. the placebo-group. In both megestrol acetate-groups, the absolute weights of the kidneys as well as the absolute weight of the quadriceps-muscle are significantly lower compared to the placebo-groups. The data for the individual weights of organs are depicted and analysed in the following.

Hearts and Lungs

Figure 6:
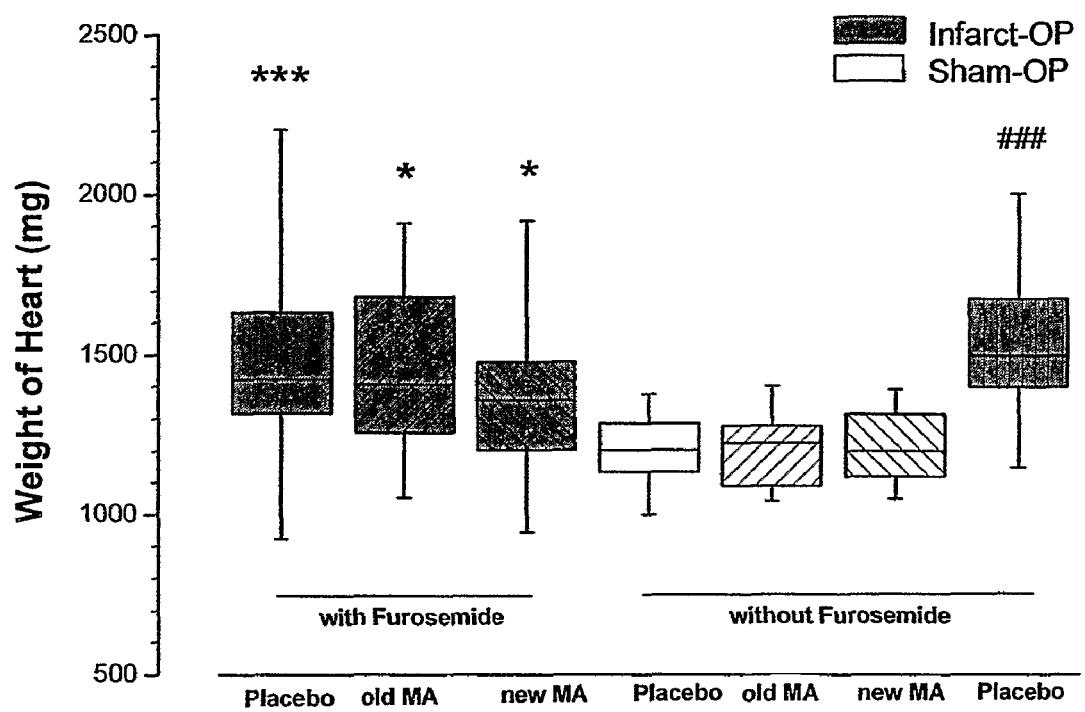
FIG. 6 shows the absolute weights of all groups. The groups received placebo, old or novel MA in the gavage and optionally furosemide in drinking water. *p<0.05 and ***p<0.001 vs. the corresponding sham-group with the same therapy in the gavage, ### p=0.0048 vs. novel megestrol acetate.
Figure 8:
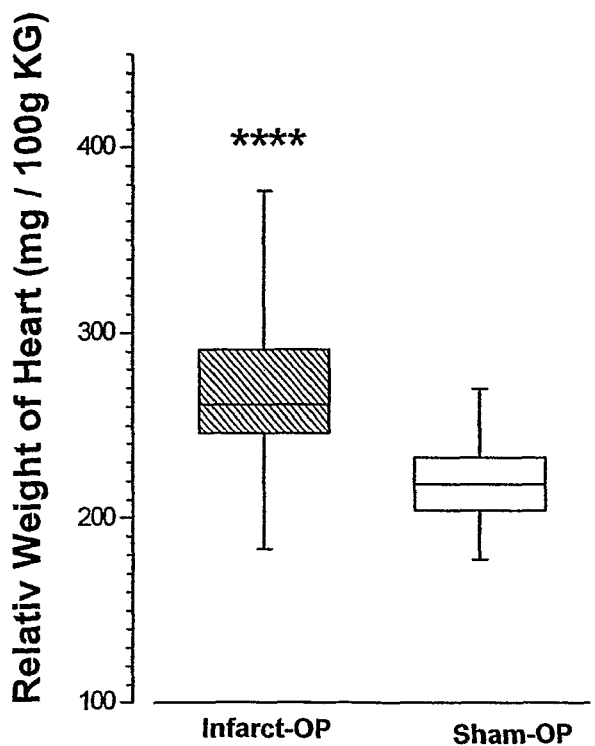
FIG. 8 shows the relative heart weights of infarction-(with furosemide) and sham-surgery (without furosemide) animals. ****p<0.0001 vs. sham-surgery.

In summary, the infarction-groups exhibited higher weights compared to the sham-surgery groups (FIG. 8 and table 6). The comparison of all infarction-with the sham-surgery groups resulted in 25% higher heart weights in the infarction-groups. FIG. 6 shows the absolute weights of all groups. The groups received placebo, old or novel MA in the gavage and optionally furosemide in drinking water. *p<0.05 and ***p<0.001 vs. the corresponding sham-group with the same therapy in the gavage, ### p=0.0048 vs. novel megestrol acetate.

Since the body size plays an important role the heart weight is put in relation thereto and given in mg per 100 g body weight. Even after relativation the infarction animals still have a 23% higher relative heart weight, compared to the sham-surgery animals (see table 6). A significant correlation of the heart weight with the size of infarction was found (heart weight and size of infarction: R=0.23, p=0.02; relative heart weight and size of infarction: R=0.30. p=0.002).

TABLE 6

Heart- and lung weights of infarction- and sham-surgery animals at the end of the observation period.

| | Infarction-Surgery n = 73 | Sham-Surgery n = 35 | p-Value |
|---|---|---|---|
| Heart Weight (mg) | 1487 ± 41 | 1211 ± 21 | <0.0001 |
| Rel. Heart Weight (mg/100 g KG) | 280 ± 7.6 | 224 ± 5.2 | <0.0001 |
| Right Atrium (mg) | 67 ± 4.6 | 40 ± 1.9 | 0.0002 |
| Left Atrium (mg) | 67 ± 4.3 | 33 ± 1.1 | <0.0001 |
| Right Ventricle (mg) | 276 ± 13.9 | 208 ± 5.8 | 0.0011 |
| Left Ventricle (mg) | 640 ± 11.4 | 589 ± 13.7 | 0.0093 |
| Lung Weight (mg)[1] | 2075 ± 92 | 1720 ± 23 | 0.0109 |

[1]Sham-surgery n = 34.

The comparison of the individual parts of the heart did also show significantly heavier parts in the infarction-groups compared to the sham-surgery animals for the heart atrium and heart chambers as well as for the lung weights (table 6).

Figure 7:
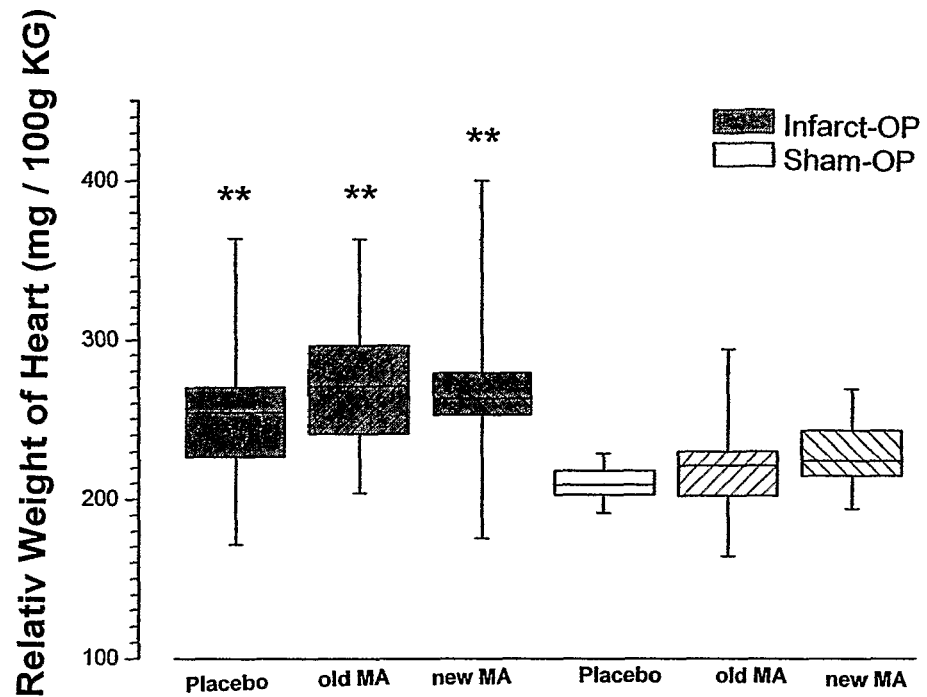
FIG. 7 shows the relative heart weights of all groups. All depicted infarction-groups with furosemide, sham-groups without furosemide. **p<0.01 vs. the corresponding sham-group.

The comparison of the relative heart weights between the individual infarction-groups is shown in FIG. 7. Statistically, there are no differences between the different infarction-groups (ANOVA p=0.52). Furthermore, the differences in the absolute heart weight (FIG. 6), left atrium and right ventricle between den individual infarction-groups and between the individual sham-surgery groups are not significant (all p>0.11). Nevertheless, the absolute heart weight in the infarction-group with novel megestrol acetate (with furosemide) is significantly lower than in the infarction-placebo-group without furosemide (Mann-Whitney-Test p=0.0048). FIG. 7 shows the relative heart weights of all groups. All depicted infarction-groups with furosemide, sham-groups without furosemide. p<0.01 vs. the corresponding sham-group. FIG. 8 shows the relative heart weights of infarction-(with furosemide) and sham-surgery (without furosemide) animals. **p<0.0001 vs. sham-surgery

TABLE 7

Mean values of the heart- and lung weights the infarction-groups at the end of the observation period.
Significant values vs. placebo are indicated with *(p < 0.05), vs. old megestrol acetate with #(p < 0.05).

| | Infarction-Placebo n = 23 | Infarction-old MA n = 24 | Infarction-novel MA n = 27 |
|---|---|---|---|
| Heart Weight (mg) | 1563 ± 89 | 1481 ± 58 | 1431 ± 62 |
| Rel. Heart Weight (mg/100 g KG) | 267 ± 13 | 283 ± 11 | 287 ± 14 |
| Right Atrium (mg) | 78 ± 11 | 67 ± 6 | 57 ± 6* |
| Left Atrium (mg) | 72 ± 7 | 70 ± 8 | 59 ± 8 |
| Right Ventricle (mg) | 294 ± 31 | 291 ± 24 | 249 ± 18 |
| Left Ventricle (mg) | 683 ± 24 | 624 ± 20* | 622 ± 14* |
| Lung Weight (mg)[1] | 2238 ± 189 | 2246 ± 183 | 1778 ± 81*# |
| rel. Lung Weight (mg/100 g KG) | 384 ± 30 | 429 ± 34 | 357 ± 18# |

Related to the infarction-placebo-group, the weight of the right atrium in the infarction-group, that was treated with the novel megestrol acetate is reduced (p=0.02). In both infarction-megestrol acetate-groups the left ventricle shows a reduced final weight (old megestrol acetate vs. placebo p=0.03, novel megestrol acetate vs. placebo p=0.02). The weight of the lung is increased in the infarction-groups with placebo and old megestrol acetate vs. novel megestrol acetate (p=0.01 novel megestrol acetate vs. placebo and p=0.01 novel vs. old megestrol acetate), see table 7. At relativation of the lung weight to the body weight, the result vs. placebo is no longer significant (novel megestrol acetate vs. placebo: p=0.45). The relativation nevertheless confirmed the increased lung weight in the group with old megestrol acetate vs. novel megestrol acetate (p=0.04).

Results

Progression of Weight

The weight increase in both infarction-megestrol acetate-groups was significantly reduced vs. the infarction-placebo-group (p<0.0001). These results are in agreement with studies that reported a reduced weight increase under megestrol acetate-therapy in male rats [Engelson E S, Pi-Sunyer F X, Kotler D P. Effects of Megestrol Acetate and Testosterone on body composition in castrated male Sprague-Dawley rats. Nutrition 1999; 15: 465-473, Williamson P S, Browning J D, MacDonald R S. Megestrol acetate increases short-term food intake in zinc-deficient rats. Physiol Behav 2002; 75: 323-330, Browning J D, MacDonald R S, Thornton W V. Reduced food intake in zink deficient rats is normalized by megestrol acetate but not by insulin-like growth factor-I. J Nutr 1998; 128: 136-142]. Tissel et al. [Tissel L E, Salander H. Androgenic properties and adrenal depressant activity of megestrol acetate observed in castrated male rats. Acta Endocrinol 1975; 78: 316-324] found an unchanged food uptake, other authors demonstrate an increased food uptake under therapy with megestrol acetate [Williamson P S, Browning J D, MacDonald R S. Megestrol acetate increases short-term food intake in zinc-deficient rats. Physiol Beliav 2002; 75: 323-330, McCarthy H D, Crowder R E, Dryden S, Williams G. Megestrol acetate stimulates food and water intake in the rat: effects on regional hypothalamic neuropeptide Y concentrations. Eur J Pharm 1994; 265: 99-102, Browning J D, MacDonald R S, Thornton W I. Reduced food intake in zinc deficient rats is normalized by megestrol acetate but not by insulin-like growth factor-I. J Nutr 1998; 128: 136-142].

The progressions of weight of the infarction-groups (all with furosemide) are not different compared to the corresponding sham-surgery groups. Since the format of oedema due to the application of furosemide is unlikely (subjectively confirmed during the experiments) it can be taken that no cachexia has developed due to the heart insufficiency.

Echocardiography and Heart Weight

The present results of the echocardiography show increased ventricles thicker posterior walls and a significantly reduced heart function in the infarction animals compared to the sham-surgery animals (see also table 3). This verifies the presence of a heart insufficiency in animals with infarction and confirms the results of other studies [Takahashi K, Ito Y, Morikawa M, et al. Adenoviral-delivered angiopoietin-1 reduces infarction and attenuates the progression of cardial dysfunction the rat model of acute myocardial infarction. Mol Ther 2003; 9: 584-592, Cittadini A, Monti M G, Isgaard J. Aldosterone receptor blockade improves left ventricular remodelling and increases ventricular fibrillation. Cardiovasc Res 2003; 58: 555-564, Francis J, Weiss R M, Wie S G, et al. Progression of heart failure after myocardial infarction in the rat. Am J Phys-Reg I 2001. 281; R1734-1745].

Under therapy with megestrol acetate an improvement of the heart function could be found. Compared to placebo following the therapy with novel megestrol acetate, the LVEF as well as the FS were echocardiographically significantly improved by 15 and 19%, respectively. Using the old megestrol acetate, the improvement of the cardinal function was only slightly less than with novel megestrol acetate. Compared to placebo the LVEF at therapy with old megestrol acetate increased by 10% and the FS by 11% (table 3), but both results were not statistically significant ($p=0.21$ and $p=0.23$, respectively). Since megestrol acetate is used for the first time in an animal study in cardiology there are no comparative studies available. Without wanting to be bound by theory, the inhibition of IL-6 could be responsible for the improved heart function.

In addition to the echocardiographically determined parameters for the heart function also the heart weight can be a further factor for the presence and the severity of a heart insufficiency. As a compensation in heart insufficiency a myocardial hypertrophy occurs, and the muscle wall is therefore heavier. The significantly lower weight the left ventricle, the main infarction area, appears to point to a better heart function in both infarction-megestrol acetate-groups. The infarction sizes did not differ between the therapy groups. In addition, a lower lung weight and a smaller right atrium in the group with novel megestrol acetate are indicators for an improved heart function.

Example 2

Furosemide-Study

The infarction-furosemide-group corresponds to the blinded infarction-placebo-group of the megestrol acetate-Study (here: infarction-furosemide-group). An additional infarction-surgery group received simple drinking water without furosemide and served as control group for the furosemide-study (here: infarction-placebo-group). In order to expose all animals to equal conditions, in this group the furosemide-study was gavaged unblinded with placebo. A further group is the sham-placebo-group, that corresponds to the blinded sham-placebo-group of the megestrol acetate-study (here: sham-placebo-group).

Progression of Weight

Like in the megestrol acetate-study, the weight values corresponding to the day post-surgery of the respective animal were compared, but this time the data was analysed as a change of weight starting from the beginning of therapy of the furosemide-study ($18^{th}$ day post-surgery=day 0 of the furosemide-study). This therefore results in a 26 days longer period of observation for the diuretic-study in comparison with the megestrol acetate-study. Furosemide was given until the end of the observation period and to removal of organs, respectively.

At the beginning of the diuretic-study (day 18 following surgery ±0.1) the animals had a mean weight of 322±3 g [n=33] in the infarction-furosemide-group and 328±4 g [n=33] in the infarction placebo-group, respectively, and 329±4 g [n=12] in the sham-surgery group. At the end of the observation period the infarction-furosemide-animals gained weight by 81% (583±12 g, n=23), the infarction-placebo-animals by 88% (618±10 g, [n=30]), and the sham-surgery animals by 72% (566±17 g [n=11]).

FIG. 9 shows the mean change of weight with standard deviation. All depicted groups received placebo in the gavage. [1]A significance (indicated by * for $p<0.05$) can be found starting from day 105 for infarction-furosemide vs. infarction-placebo. [2]The analysis only contained animals that survived until the end of the study: infarction-furosemide: 23 of 39, infarction-placebo 30 of 33, sham-placebo 12 of 12.

The changes of weight of the infarction-surgery test cohorts that were treated with furosemide and placebo (drinking water), respectively, are depicted for the whole duration of the therapy in FIG. 9. For a comparison, the sham-surgery animals that were treated with placebo are also depicted in the FIG. 9. The latter have a significantly reduced progression of weight compared with the infarction-animals without diuretic ($p=0.0021$).

In den both infarction-groups, an increase of weight over the whole period of time can be found. The furosemide-group showed a less pronounced progress in comparison with the placebo-group with infarction starting from day 105 after beginning of therapy, this difference is significant (FIG. 9).

Seen over the whole period of time, the infarction-placebo-animals with 1.5 g/day exhibited the largest increase of weight, followed by the infarction-furosemide-group with 1.4 g/day and den sham-surgery animals with 1.3 g/day. In the animals without diuretic, subjectively oedema were seen, which could explain the larger increase of weight.

Echocardiography

Between the infarction-surgery groups with and without furosemide no differences could be found in the echocardiographically determined parameter. The echocardiographic heart function parameters LVEF and FS for both infarction groups are worse vs. the sham-surgery group (p<0.0001, see table 8).

TABLE 8

Echocardiographically determined parameters
for the groups of the furosemide-Study
(all indicated groups with placebo in the gavage).
The infarction-furosemide-group received furosemide
via the drinking water, both mentioned placebo-groups
received drinking water without supplements.

|  | sham-placebo n = 10 | infarction-furosemide n = 20 | infarction-placebo n = 30 |
|---|---|---|---|
| LVEDD (cm) | 0.83 ± 0.02 | 1.06 ± 0.02**** | 1.06 ± 0.01**** |
| LVESD (cm) | 0.45 ± 0.04 | 0.90 ± 0.02**** | 0.89 ± 0.02**** |
| LVHW d (cm) | 0.17 ± 0.01 | 0.17 ± 0.01 | 0.18 ± 0.004 |
| IVS d (cm) | 0.14 ± 0.01 | 0.13 ± 0.03 | 0.10 ± 0.004 |
| FS (%) | 41.1 ± 3.0 | 15.1 ± 1.0**** | 15.8 ± 0.7**** |
| LVEF (%) | 75.8 ± 4.0 | 35.5 ± 2.0**** | 37.0 ± 1.4**** |
| E (m/s) | 0.78 ± 0.04 | 0.84 ± 0.03 | 0.78 ± 0.03 |
| A (m/s) | 0.60 ± 0.05 | 0.62 ± 0.05 | 0.49 ± 0.04 |
| E:A | 1.39 ± 0.16 | 1.61 ± 0.21 | 1.85 ± 0.14 |

LVEDD: left ventricular end-diastolic diameter,
LVESD: left ventricular end-systolic diameter
LVHW: left ventricular posterior wall,
IVS: inter-ventricular septum,
d: end-diastolic,
FS: fractional shortening (left ventricular),
LVEF: left ventricular ejection fraction,
E:A: Effect profile over the mitral valve. Significant values vs. sham-placebo are indicated with **** for p < 0.0001.

Progression of Weight

In the furosemide-study the largest increase of weight was found in the infarction-placebo-group (without furosemide) (p<0.05 starting from day 105 vs. infarction-furosemide-group and p=0.0021 vs. sham-placebo-group).

Echocardiography

The results show that furosemide has no direct effect on the echocardiographically determined heart function.

The invention claimed is:

1. A method for improving cardiac function and/or the treatment of chronic heart insufficiency in a mammal, wherein said method consists of administering to said mammal an effective amount of megestrol acetate or a pharmaceutically acceptable salt thereof in combination with a diuretic agent, and, optionally, one or more agents selected from the group consisting of vasodilators, digitalis, ACE-inhibitors, angiotensin-II receptor antagonists, beta-blockers, endothelin receptor antagonists, xanthin oxidase inhibitors, statins (HMG-CoA reductase inhibitors), bile-acid resins, cholesterol absorption inhibitors, nicotinic acid, and fabric acid derivatives.

2. The method, according to claim 1, wherein said mammal is a human.

3. The method, according to claim 1, wherein said megestrol acetate is selected from a megestrol acetate oral suspension and/or a microcrystalline formulation of a megestrol acetate oral suspension.

4. The method, according to claim 1, wherein said chronic heart insufficiency is resulting from a -cardiomyopathy.

5. The method, according to claim 4, wherein said chronic heart insufficiency is resulting from a cardiomyopathy due to myocardial infarction.

6. The method, according to claim 1, wherein said effective amount of megestrol acetate or pharmaceutically acceptable salt thereof is applied orally.

7. The method, according to claim 1, wherein said megestrol acetate or a pharmaceutically acceptable salt thereof is applied in a dosage of between 30 mg/d and 2000 mg/d.

8. The method, according to claim 1, wherein said megestrol acetate or a pharmaceutically acceptable salt thereof is applied in a dosage of between 4 and 15 mg/kg/d.

9. The method, according to claim 7, wherein said megestrol acetate or a pharmaceutically acceptable salt thereof is applied in a dosage of between 100 mg/d and 1600 mg/d.

10. The method, according to claim 7, wherein said megestrol acetate or a pharmaceutically acceptable salt thereof is applied in a dosage of between 300 mg/d and 800 mg/d.

11. The method, according to claim 1, wherein said diuretic agent is furosemide.

12. A method for improving cardiac function and/or the treatment of chronic heart insufficiency in a mammal, wherein said method consists of administering to the mammal an effective amount of megestrol acetate or a pharmaceutically acceptable salt thereof in combination with a diuretic agent.

13. The method, according to claim 12, wherein said mammal is a human.

14. The method, according to claim 12, wherein said megestrol acetate is selected from a megestrol acetate oral suspension and/or a microcrystalline formulation of a megestrol acetate oral suspension.

15. The method, according to claim 12, wherein said chronic heart insufficiency is resulting from a cardiomyopathy.

16. The method, according to claim 12, wherein said chronic heart insufficiency is resulting from a cardiomyopathy due to myocardial infarction.

17. The method, according to claim 12, wherein said effective amount of megestrol acetate or a pharmaceutically acceptable salt thereof is applied orally.

18. The method, according to claim 12, wherein said megestrol acetate or a pharmaceutically acceptable salt thereof is applied in a dosage of between 30 mg/d and 2000 mg/d.

19. The method, according to claim 1, wherein said megestrol acetate or a pharmaceutically acceptable salt thereof is applied in a dosage of between 4 and 15 mg/kg/d.

* * * * *

UNITED STATES PATENT AND TRADEMARK OFFICE
CERTIFICATE OF CORRECTION

PATENT NO. : 8,383,612 B2
APPLICATION NO. : 11/667899
DATED : February 26, 2013
INVENTOR(S) : Stefan Anker It is certified that error appears in the above-identified patent and that said Letters Patent is hereby corrected as shown below:

In the Specifications

Column 2,
Lines 55-56, "[Komblinth AB" should read --[Kornblinth AB--

Column 13,
Line 24, "parastemal" should read --parasternal--

In the Claims

Column 21,
Line 51, "fabric acid" should read --fibric acid--

Column 22,
Line 6, "a -cardiomyopathy" should read --a cardiomyopathy--

Signed and Sealed this
Twenty-eighth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,383,612 B2  Page 1 of 1
APPLICATION NO. : 11/667899
DATED : February 26, 2013
INVENTOR(S) : Stefan Anker It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this
First Day of September, 2015

Michelle K. Lee
*Director of the United States Patent and Trademark Office*